United States Patent
Kim et al.

(10) Patent No.: US 9,869,616 B2
(45) Date of Patent: Jan. 16, 2018

(54) HYDROGEL ENCAPSULATED CELL PATTERNING AND TRANSFERRING METHOD AND CELL-BASED BIOSENSOR USING THE SAME

(71) Applicant: UNIST ACADEMY-INDUSTRY RESEARCH CORPORATION, Ulsan (KR)

(72) Inventors: Taesung Kim, Ulsan (KR); Woon Sun Choi, Ulsan (KR)

(73) Assignee: UNIST (ULSAN NATIONAL INSTITUTE OF SCIENCE AND TECHNOLOGY), Ulsan (KR)

( * ) Notice: Subject to any disclaimer, the term of this patent is extended or adjusted under 35 U.S.C. 154(b) by 129 days.

(21) Appl. No.: 14/353,032

(22) PCT Filed: Oct. 18, 2012

(86) PCT No.: PCT/KR2012/008545
§ 371 (c)(1),
(2) Date: Apr. 21, 2014

(87) PCT Pub. No.: WO2013/058572
PCT Pub. Date: Apr. 25, 2013

(65) Prior Publication Data
US 2014/0242632 A1 Aug. 28, 2014

(30) Foreign Application Priority Data
Oct. 19, 2011 (KR) .................. 10-2011-0106977

(51) Int. Cl.
*G01N 1/30* (2006.01)
*G01N 33/543* (2006.01)
(Continued)

(52) U.S. Cl.
CPC ............ *G01N 1/30* (2013.01); *G01N 33/5436* (2013.01); *B81C 1/0046* (2013.01); *C08L 5/04* (2013.01);
(Continued)

(58) Field of Classification Search
CPC ... G01N 1/30; G01N 33/5436; G01N 2500/10
(Continued)

(56) References Cited

U.S. PATENT DOCUMENTS

2006/0173394 A1* 8/2006 Stroock ............... A61F 2/30756
602/41
2006/0223165 A1 10/2006 Chang et al.

FOREIGN PATENT DOCUMENTS

KR  10-2005-0009612 A   1/2005
KR    10-081153231 B1   1/2008
(Continued)

OTHER PUBLICATIONS

Rago (2009). Encapsulated Arrays of Self-Assembled Microtissues: An Alternative to Spherical Microcapsules. Tissue Engineering Part A, v15(2), p. 387-395.*
(Continued)

*Primary Examiner* — Sean C. Barron
(74) *Attorney, Agent, or Firm* — Revolution IP, PLLC

(57) ABSTRACT

Provided are a hydrogel-encapsulated cell patterning and transferring method comprising: preparing a substrate having a hydrogel-encapsulated cell patterning comprising a first cell and an alginate hydrogel; preparing an agarose hydrogel substrate comprising agarose hydrogel and any one of a second cell and a physiological active substance; and disposing the substrate having the hydrogel-encapsulated cell patterning on the agarose hydrogel substrate and transferring the cell patterning and a biosensor comprising: a first substrate having a hydrogel-encapsulated cell patterning
(Continued)

comprising a first cell and an alginate hydrogel; and an agarose hydrogel second substrate comprising agarose hydrogel and any one of a second cell and a physiological active substance.

6 Claims, 6 Drawing Sheets

(51) Int. Cl.
*B81C 1/00* (2006.01)
*C08L 5/04* (2006.01)

(52) U.S. Cl.
CPC ...... *C12N 2533/74* (2013.01); *C12N 2533/76* (2013.01); *G01N 2500/10* (2013.01)

(58) Field of Classification Search
USPC .......................................................... 435/29
See application file for complete search history.

(56) References Cited

FOREIGN PATENT DOCUMENTS

| | | | |
|---|---|---|---|
| KR | 10-2011-0027366 A | 3/2011 | |
| KR | 10-2011-0028019 A | 3/2011 | |
| WO | WO-0124842 A2 * | 4/2001 | ........... A61K 9/0024 |
| WO | WO-2007087402 A2 * | 8/2007 | ........... C12N 5/0012 |

OTHER PUBLICATIONS

Choi et al. Patterning and transferring hydrogel-encapsulated bacterial cells for quantitative analysis of synthetically engineered genetic circuits. Biomaterials, v33 (epub. Oct. 19, 2011), p. 624-633.*

McGuigan et al. Cell Encapsulation in Sub-mm Sized Gel Modules Using Replica Molding. PLoS One, v3(5) e2258, p. 1-11.*

* cited by examiner

[FIG. 1]
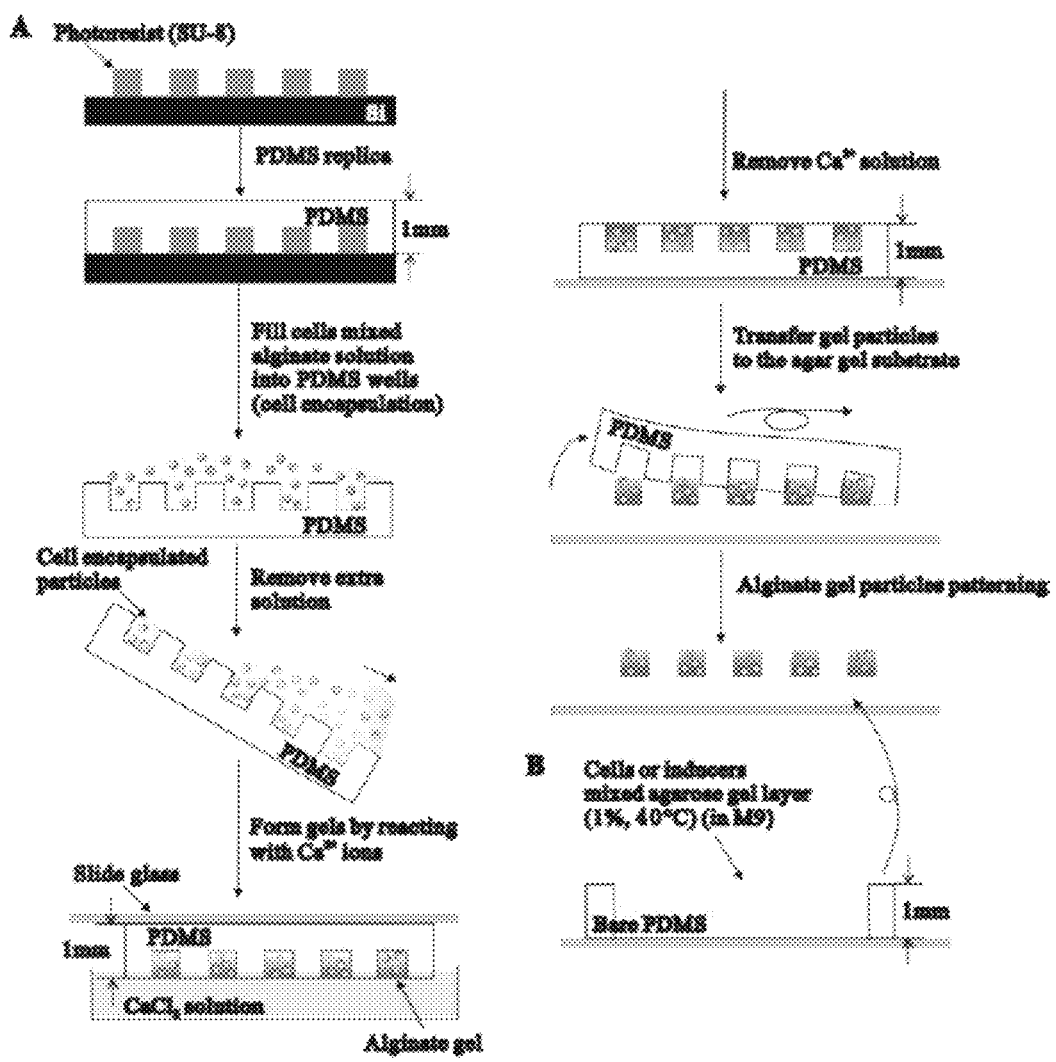

[FIG. 2]
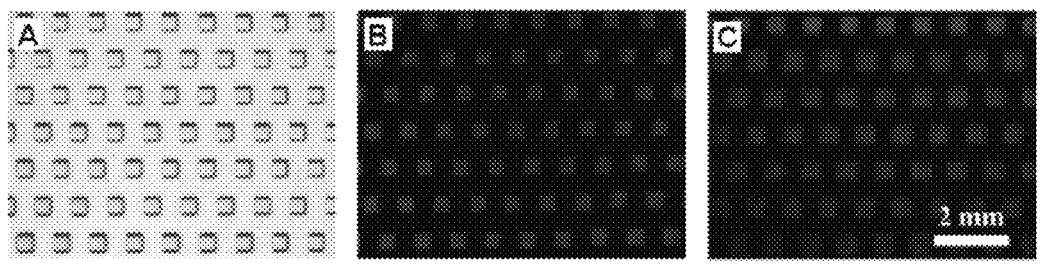
[FIG. 3]
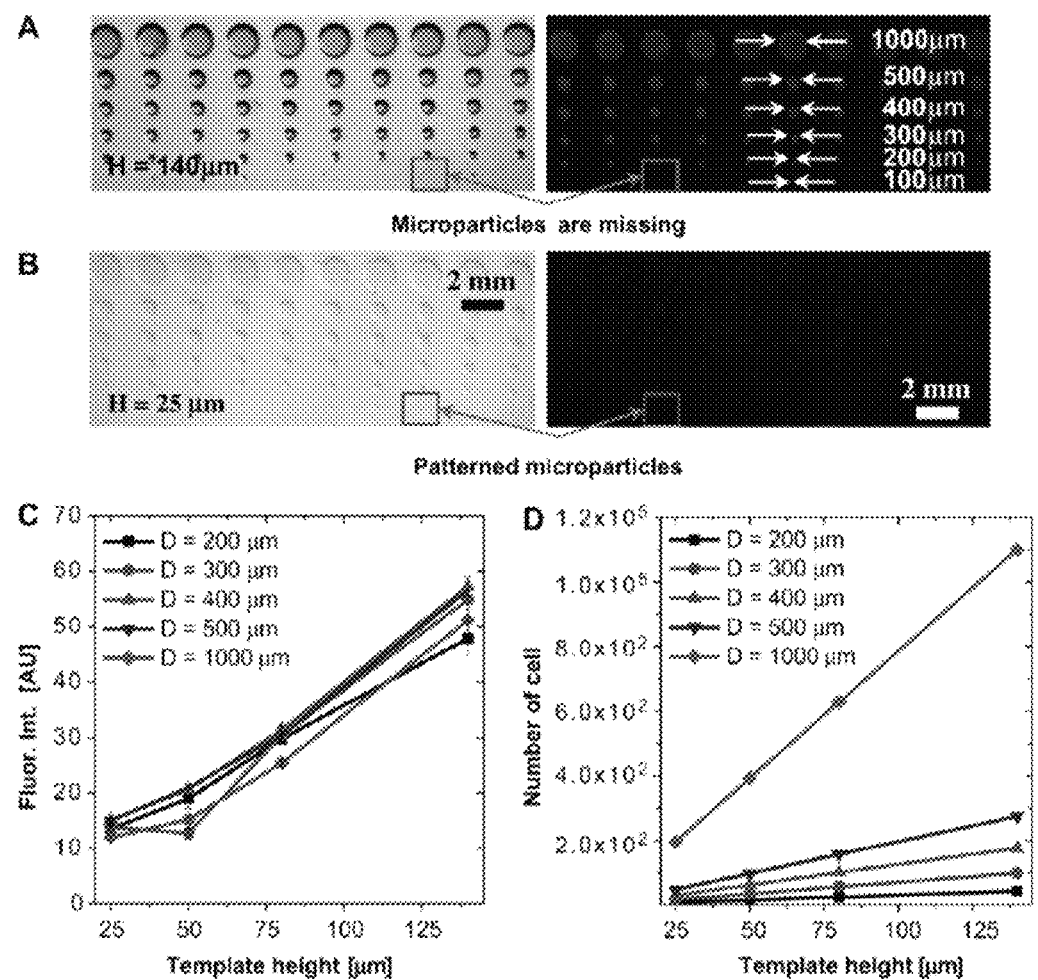

[FIG. 4]
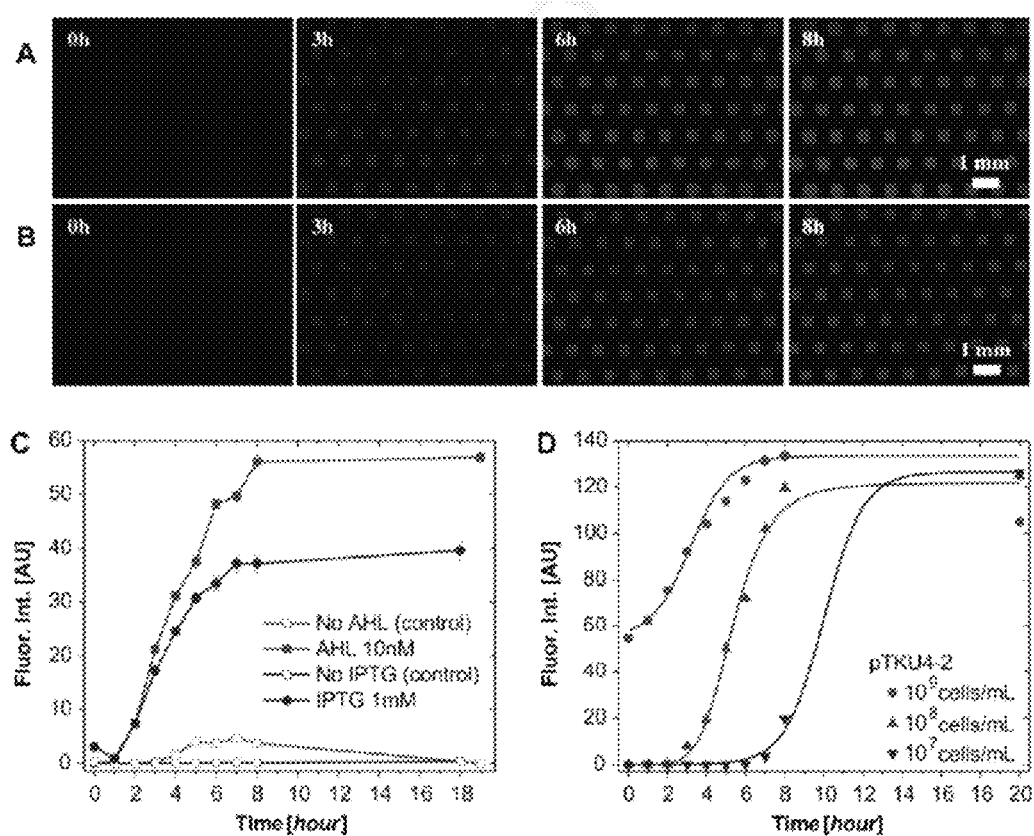

[FIG. 5]
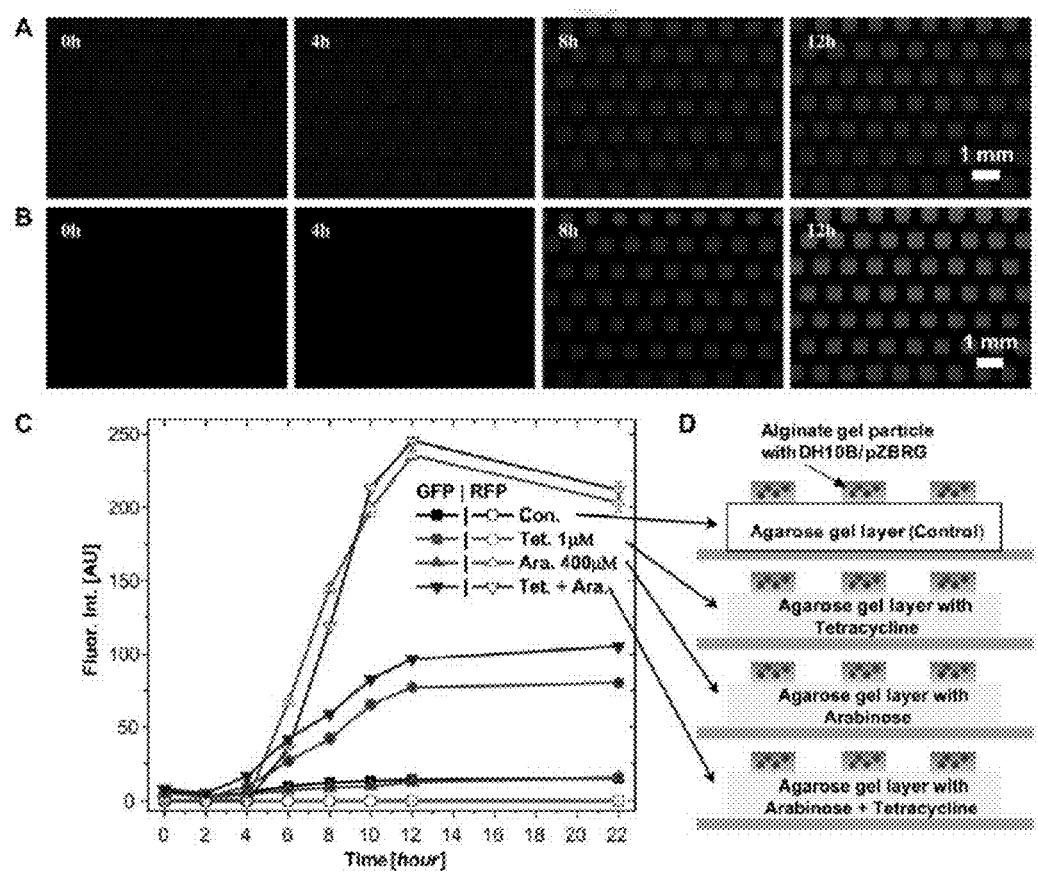

[FIG. 6]
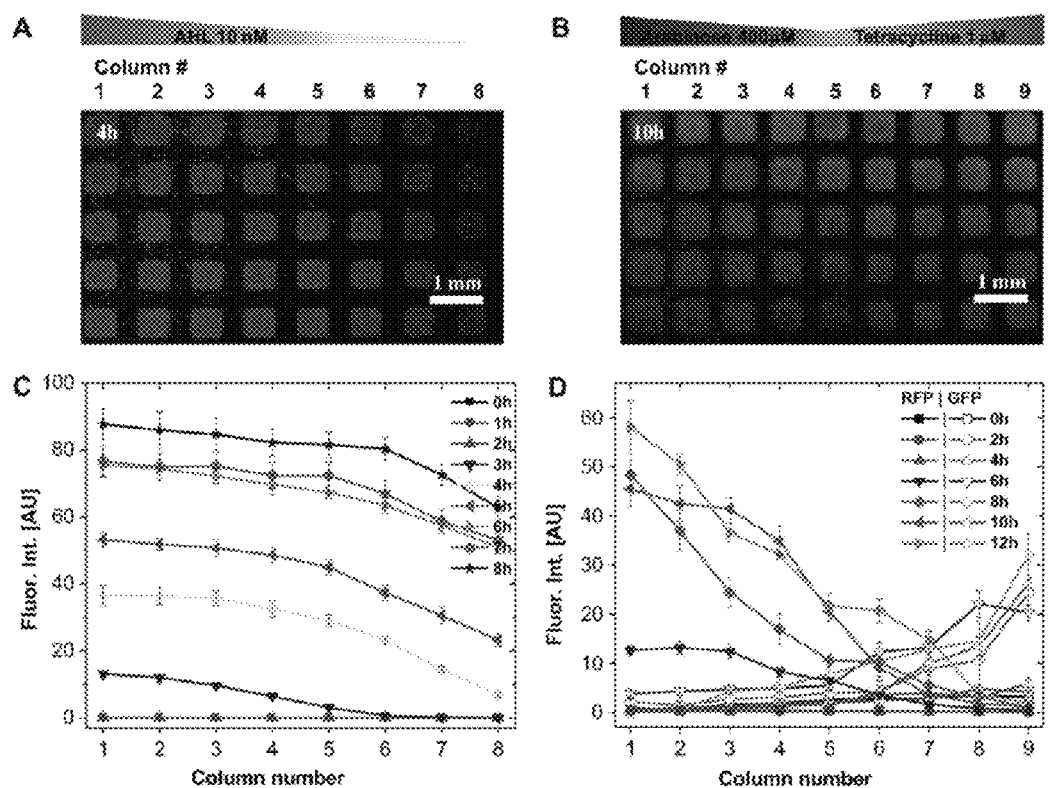

[FIG. 7]
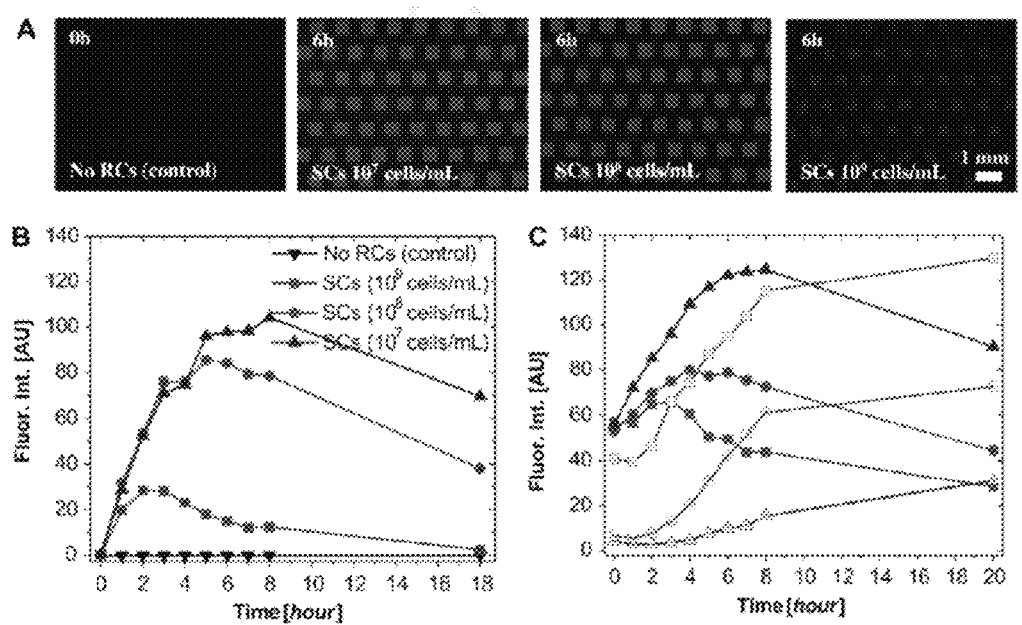

HYDROGEL ENCAPSULATED CELL PATTERNING AND TRANSFERRING METHOD AND CELL-BASED BIOSENSOR USING THE SAME

CROSS REFERENCE TO PRIOR APPLICATIONS

This application is a National Stage Application of PCT International Patent Application No. PCT/KR2012/008545 filed on Oct. 18, 2012, under 35 U.S.C. §371, which claims priority to Korean Patent Application No. 10-2011-0106977 filed on Oct. 19, 2011, which are all hereby incorporated by reference in their entirety.

TECHNICAL FIELD

The present invention relates to a hydrogel encapsulated cell patterning and transferring method and a cell-based biosensor using the same.

BACKGROUND ART

Cell patterning is to fix various cells on particular sites at a micrometer level, provides a model system for studies on basic cell biology, such as cell to cell, cell to surface, or cell to matrix communication, and is also required to manufacture cell sensors. That is, recently, the necessity of cell sensors is emphasized in a reduction in costs for assay, diagnosis and the development of novel drugs, and high throughput screening for achieving high efficiency, and thus, studies on arraying and miniaturizing a cell sensor by cell patterning are actively being performed.

Micro-patterned cell arrays are fabricated by applying a typical semiconductor fabrication technology, such as a micro electro mechanical system (MEMS), in compliance with requirements of bio and medical fields. Up to now, a method of manufacturing cell array, including micro-patterning a 2-dimensional surface of metal or plastic by photolithography and soft lithography and then selectively adhering cells on the patterned surface and controlling growth thereof, is widely used.

Meanwhile, together with cell patterning, transferring a cell-patterned substrate to other substrates may contribute to fabrication of DNA chips or protein chips that require great quantities of sample arrays by using a peptide or biopolymer or DNA, screening test for generic diseases, studies on cross-talks between proteins, and development of novel drugs, and based on this, patterning cells or biomolecules on a substrate are applied in various fields, such as cell biology, antimicrobial agent screening, antimicrobial monitoring, or tissue engineering. However, studies on transferring of patterned cells to other substrates are not yet sufficient.

Accordingly, the inventors of the present application studies cell patterning and transferring formed cell patterns onto other substrates, and found that a substrate having hydrogel-encapsulated cell patterning including alginate hydrogel can be transferred onto an agarose hydrogel substrate and completed the present invention.

DETAILED DESCRIPTION OF THE INVENTION

Technical Problem

The present invention provides a cell patterning method and a cell transferring method of transferring a cell patterning onto another substrate.

The present invention also provides a platform technology required to develop a cell-based biosensor by using the methods.

Technical Solution

According to an aspect of the present invention, a hydrogel-encapsulated cell patterning and transferring method (HPT) includes: preparing a substrate having a hydrogel-encapsulated cell patterning including a first cell and an alginate hydrogel; preparing an agarose hydrogel substrate including agarose hydrogel and any one of a second cell and a physiological active substance; and disposing the substrate having the hydrogel-encapsulated cell patterning on the agarose hydrogel substrate and transferring the cell patterning.

According to another aspect of the present invention, a biosensor includes: a first substrate having a hydrogel-encapsulated cell patterning including a first cell and an alginate hydrogel; and an agarose hydrogel second substrate including agarose hydrogel and any one of a second cell and a physiological active substance.

Advantageous Effects

When a HPT method according to embodiments of the present invention is used, secreted materials of patterned cells and a protein expressed inside cell can be quantitatively analyzed, and since small quantities of cells and biomolecules are patterned in micrometer-sized individual spaces with high accuracy, real-time monitoring of cell state and high-throughput screening can be performed, and ultimately, the method may substantially contribute to assay and diagnosis of a cell-based biosensor, and a decrease in costs and labor force for the development of novel drugs, and high efficiency of high throughput screening. In addition, a biosensor according to the present invention is used to evaluate intercellular signals and is also used as a multiple assay material biosensor.

DESCRIPTION OF THE DRAWINGS

FIG. 1 illustrates a microfabrication process for a hydrogel-encapsulated cell patterning and transferring method (HPT).

FIGS. 2A to 2C show monitoring results of alginate hydrogel-encapsulated cells;

FIGS. 3A to 3D show patterning and transferring characteristics of alginate hydrogel-encapsulated cells.

FIGS. 4A to 4D show quantitative analysis results of cell response (gene expression level) through extracelluar induction using the HPT according to the present invention.

FIGS. 5A to 5C show quantitative analysis results of multiple foreign material screening and cross-talk between genes, using cells having 2 generic circuits by using a HPT according to the present invention, and FIG. 5D illustrates an agarose gel particle layer used in the HPT according to the present invention.

FIGS. 6A to 6D shows assay results of gene expression in the presence of various concentrations of inducer obtained by using the HPT according to the present invention.

FIGS. 7A to 7D show assay results of cell communications obtained by using the HPT according to the present invention.

MODE OF THE INVENTION

According to an aspect of the present invention, a hydrogel-encapsulated cell patterning and transferring method (HPT) includes: preparing a substrate having a hydrogel-encapsulated cell patterning including a first cell and an alginate hydrogel; preparing an agarose hydrogel substrate including agarose hydrogel and any one of a second cell and a physiological active substance; and disposing the substrate having the hydrogel-encapsulated cell patterning on the agarose hydrogel substrate and transferring the cell patterning.

The substrate having the hydrogel-encapsulated cell patterning may be prepared as follows: forming a mold having a photosensitive resin on a substrate by soft lithography; preparing a mold having a shape corresponding the formed mold, followed by pouring a polymer thereinto and heat treating the result so as to form a polymer mold; filling the polymer mold with cells mixed with an alginate hydrogel solution; tilting the polymer mold to remove the excess of the solution; and gelating the obtained alginate hydrogel pattern by immersing the alginate hydrogel pattern in a calcium solution.

The method according to an embodiment of the present invention may further include, after the polymer mold is prepared, treating the polymer mold with oxygen plasma.

The substrate used in embodiments of the present invention may be formed of any one selected from the group consisting of silicon, glass, and methacrylate resin (PMMA), and a material for forming the substrate is not limited thereto, and any one of various substrate materials that are typically used in the art may be used herein.

The photosensitive resin used in embodiments of the present invention may be any one of various photosensitive resins that are typically used for lithography, and for example, SU-8 may be used as the photosensitive resin, but is not limited thereto.

The polymer used in embodiments of the present invention may be polydimethylsiloxane (PDMS), or the like, but is not limited thereto, and other polymers may instead be used herein.

The cells mixed with the alginate hydrogel solution are poured into the polymer mold to fill patterned microwells of which length ranged from 100 μm to 1000 μm.

The first cell and the second cell used in embodiments of the present invention may each be selected from the group consisting of an epithelial cell, a neural cell, an epidermal cell, a keratin cell, a hematoblast, a melanin cell, a chondrocyte, a lymphocyte (B and T lymphocyte), a red blood cell, a macrophage, a monocyte, a mononuclear cell, a fibroblast, a cardiomyocyte, and other muscular cell, but are not limited thereto.

The physiological active substance used in embodiments of the present invention may include acetylhomoserine lactone (AHL), isopropyl-beta-D-thiogalactopyranoside (IPTG), tetracycline, arabinose, or the like, but is not limited thereto.

In addition, the present invention provides a biosensor including: a first substrate having a hydrogel-encapsulated cell patterning including a first cell and an alginate hydrogel; and an agarose hydrogel second substrate including agarose hydrogel and any one of a second cell and a physiological active substance.

In this regard, the cell patterning of the first substrate may be transferred onto the second substrate.

MODE OF THE INVENTION

Hereinafter, embodiments of the present invention are described in detail.

The present invention relates to a HPT method and a cell-based biosensor using the HPT method. The cell-based biosensor is used to identify a target material included in a substrate with cells, and is prepared by mixing a target material (including a cell) to be detected with hydrogel to form a substrate and attaching patterned cells on the substrate to identify responses of the cells.

In detail, the biosensor may fix cells and physiological active substances on particular sites at a micrometer level by using a cell patterning and transferring method using a sensor substrate using hydrogel (agarose hydrogel) and a hydrogel microparticle (alginate hydrogel microparticle).

The hydrogel substrate may form concentration gradients of various chemical materials, and may enable identification of cell response according to the kind and concentration of chemical materials, such as a material with which cells react (inducer) and toxic materials.

The cell patterning and transferring method using hydrogel microparticles may be performed by photolithography, which is suitable for repeatedly forming the same particular structure, and soft lithography for combining the particular structures with a polymer suitable for biology test to manufacture a microstructure.

For example, a picture is printed on a transparent film by using a fine laser printer to produce a mask, and ultraviolet (UV) light is irradiated to the mask so as to transfer the image of the picture onto a photosensitive resin (photosensitive negative polymer), which has been formed by coating on a silicon surface in advance to produce a mold having a shape corresponding to the picture formed by the printer, and polydimethyl siloxane (PDMS) is poured to the prepared template and heat treated at 65° C. to form a PDMS mold, and alginate hydrogel microparticles are molded using the mold to form various patterns.

The cell patterning method according to an embodiment of the present invention is a combination of fixing cells inside 3-dimensional hydrogel micropatterns, that is, a cell encapsulation technology, and a microfabrication technology.

Meanwhile, the hydrogel used in embodiments of the present invention is a material that has a 3-dimensional hydrophilic polymer network structure that is not soluble in water and that contains a great quantity of water in an aqueous solution to inflate, and when it contains a great quantity of water, the hydrogel shows very similar properties to those of biological tissues, so that when used as a biological material, its effects on surrounding cells or tissues may be minimized.

In addition, transparent characteristics of hydrogel enable various optical analyses. For example, when a fluorescent material is added to enzyme-combined hydrogel, biochemical responses occurring inside the hydrogel may be detected.

A water content of the hydrogel prepared in embodiments of the present invention may be similar to that in actual body tissues in which cells exist, and may be controlled in a range of 70 to 80%, and various proteins or physiological active substances are combined with hydrogel to make optimal conditions for cell growth.

As shown in FIG. 4, the HPT method according to an embodiment of the present invention is very useful to analyze the behavior/expression level of various generic circuits in various strains with high accuracy, and would also be further applied to the study of the extracellular responses of cells toward drugs, toxicity, antibiotics, etc. In addition, as shown in FIG. 5, the HPT method according to an embodiment of the present invention is useful to detect multiple foreign materials using cells having 2 generic circuits and to quantitatively analyze cross-talk between genes. Also, as shown in FIG. 6, the HPT method according to an embodiment of the present invention enables not only quantification of inducer concentration-dependent gene expression of generic circuits, but also analysis of cross-talk under various concentrations of inducers. In addition, as illustrated in FIG. 7, the HPT method according to an embodiment of the present invention enables cell to cell communication assay between two symbiotic-engineered cells.

Hereinafter, the present invention is described in detail with reference to the following examples. However, the present invention is not limited to the examples.

<Example 1> *Escherichia coli* Strains, Plasmids, and Culture Conditions

As shown in Table 1, this experiment was performed using two types of *Escherichia coli* strains MG1655 and DH10B. Competent cells of the MG1655 and DH10B were transformed with synthetically engineered genetic circuits. Some plasmids were transferred from the Registry of Standard Biological Parts, and the others were constructed in the experiment with different antibiotic resistance marker genes. For the growth of these strains, each *Escherichia coli* culture was grown overnight on M 9 agar solid medium plates with appropriate antibiotics at 35° C. A single colony was used to inoculate 5 mL M9 media with 1% glucose, 1% tryptone, and either 100 µg/mL ampicillin or 30 µg/mL chloramphenicol. Thereafter, the cultures were then grown overnight (16 hours) with vigorous aeration (200 rpm in a rotary shaker), and $OD_{600}$=1.5-2 cells (1-2 mL) were centrifuged at 5000 rpm for 5 min. The obtained pellet was resuspended with fresh M9 media to give bacterial suspensions with desired cell densities.

TABLE 1

| | Strain/plasmid | Description/genotype | Reference/source |
|---|---|---|---|
| Strain | *E. coli* MG 1655 | Wild-type | Anal Chem 2010; 82: 2900-6 |
| | *E. coli* DH10B | F-mcrAΔ(mrr-hsdRMS mcrBC) φ80dlacZΔM15ΔlacX74deoR recA1 araΔ139 Δ(ara leu)7697 galU galK λ⁻rpsL endA1 nupG Str$^r$ | Life Technology |
| Plasmids | pTKU4-2 | Cm$^r$; pBR322 replicon, $P_L$tetO-1-gfp | |
| | pTKU4-65 | Cm$^r$; pBR322 replicon, $P_L$tetO-1-gfp | |
| | PTKU1-11S | Cm$^r$; pBR322 replicon, $P_L$tetO-1-gfp | |
| | pTKU1-12R | Cm$^r$; pBR322 replicon, $P_L$tetO-1-gfp | |
| | pZBRG | Cm$^r$; pZB::($P_{BAD}$-rfp and $P_{tet}$-gfp) | |
| | pZB | Cm$^r$; p15A replicon, $P_{BAD}$ promoter, $P_{tet}$ promoter | J Bacteriol 2005; 187: 2793-800 |
| | pTrc99A-gfp | Cm$^r$; pBR322 replicon, $P_L$tetO-1-gfp | Appl Environ Microbiol 2005; 71: 6856-62 |

<Example 2> Fabricating Hydrogel-Encapsulated Cell Patterns

As shown in FIG. 1, the soft-lithography technology was used to fabricate an SU-8 (MicroChem Corp, 2150, 2050, and 2025, Newton, Mass., USA) mold on a silicon wafer with different thicknesses (25 µm, 50 µm, 80 µm, and 140 µm), and then about 1-mm thick PDMS replica of the mold was produced as reported in a literature. The PDMS surfaces were treated with oxygen plasma (Cute-MP, FemtoScience, Korea) under 70 W and 50 sccm of oxygen for 50 seconds to change the hydrophobic surface to the hydrophilic to better fill the patterned microwells with a hydrogel solution.

The hydrogel solution was prepared by mixing sodium alginate (1% w/v, SigmaeAldrich) and necessary nutrients (1% glucose and 1% tryptone or 4% glycerol and 1% tryptone) in M9 media. After the alginate hydrogel solution was additionally mixed with living bacterial cells, the mixture was poured onto the PDMS replica/template surface to fill the patterned microwells of which characteristic length ranged from 100 µm to 1000 µm. The excess of the solution was removed by tilting the substrate and using a blade to sweep. Subsequently, the alginate hydrogel patterns were slightly immersed in a 0.2M $CaCl_2$ solution to make them solidified.

<Example 3> Transferring Hydrogel-Encapsulated Cell Patterns onto the Other Hydrogel Substrate A PDMS frame was made on a glass slide to produce a hydrogel substrate on which the hydrogel-encapsulated cell patterns were transferred as shown in FIG. 1. A 1-mm thick PDMS slab was put on a glass slide, and the center area was cut and made empty to prepare a PDMS frame with a size of 2 cm×2 cm. An agarose hydrogel solution was prepared by mixing agarose (1% w/v), glucose (1% w/v), and tryptone (1% w/v) into M9 media and then additionally mixed with inducers or cells at 40° C. However, when arabinose was used as an inducer, glucose was substituted with glycerol (4% w/v) to avoid catabolic repression. Subsequently, the mixture was immediately cast into the PDMS frame and left at room temperature (24° C.) for gelation. After the frame was removed from the glass slide, the prepared PDMS template with hydrogel-encapsulated cell patterns was laid on the agarose hydrogel substrate. In 3-5 minutes, the PDMS template was peeled off with the cell patterns left on the agarose substrate.

This process was possible because the adhesion force between alginate hydrogel and agarose hydrogel was strong enough to transfer the alginate hydrogel patterns/particles in the PDMS template onto the agarose substrate, and when other hydrogel is used, the transferring of cell patterning does not occur.

<Example 4> Microscopy and Data Processing

The images of cell patterns were taken using a stereomicroscope (SZX16, Olympus, Japan) equipped with a CCD camera (DP72, Olympus, Japan) and a fluorescent light source (Xcite-200, ExFo Photonics solutions Inc., Mississauga, Canada) operated by the DP2-BSW software (Olympus, Japan). Cell patterns were exposed to UV lights for fluorescent imaging for 0.02-2 seconds for GFP and for 1-2 seconds for RFP. All image processing and quantification of fluorescent intensities were performed using Image J. (NIH, USA), and then results were plotted using Origin 7.1 (OriginLab, Northampton, Mass., USA).

<Example 5> Assay Results of Hydrogel Cell Patterning and Transferring

1. Characterization of Hydrogel-Encapsulated Cell Patterns the HPT method was tested by using a PDMS template in which 500 µm×500 µm square patterns are microfabricated and equidistant from each other by 500 µm. As shown in FIG. 1, a 140-µm deep PDMS template was filled with an alginate solution mixed with cells and then transferred onto an agarose hydrogel substrate on a glass slide. After the PDMS template was peeled off, the cells were monitored. The monitoring results are shown in FIGS. 2A to 2C. The bright light image of the alginate patterns on the agarose substrate that contained only nutrients appears clear (FIG. 2A), and their fluorescent image shows well organized cell patterns (FIG. 2B). The fluorescent signals are produced by the cells with pTKU4-2 plasmids that constitutively express GFP. In the same manner, the other cells with pZBRG plasmids were patterned and transferred on the agarose hydrogel substrate that contained 400 mM arabinose as an inducer so that they were activated to express red fluorescent protein (RFP) in 8 hours (FIG. 2C).

The patterning and transferring processes may limit the feature size of hydrogel microparticles forming a pattern so that the HPT method is further studied. SU-8 molds were microfabricated with different heights (H=140 µm, 80 µm, 50 µm, and 25 µm) but all the PDMS templates produced from the molds form the same array of circular patterns, and the patterns had diameters (D) of 1000 µm, 500 µm, 400 µm, 300 µm, 200 µm, and 100 µm (FIGS. 3A and 3B). For example, for the deepest PDMS template (H=140 µm), the microparticles of which diameter is greater than 200 µm are very clear in both the bright light and its corresponding fluorescent image, while the microparticles in 100 µm diameter were not successfully patterned and transferred as indicated with arrows in FIG. 3A. On the other hand, for the shallowest PDMS template (H=25 µm), all microparticles appear to be well patterned and transferred.

As a results, the process depends on the aspect ratio (AR=D/H) of microparticles. For H=140 µm and H=80 µm, only microparticles in 100 µm diameter failed in patterning and transferring so that it was confirmed that the process is guaranteed when the aspect ratio is greater than AR=1.25, where D=100 µm and H=80 µm.

In addition, from this experiment, it was confirmed that the number of cells to pattern and transfer is adjustable. For example, the density of cells in the alginate solution was $10^9$ cells/mL prior to the patterning and transferring process. Since the volume of the microparticles ranges from 0.20 nL (D=100 µm and H=25 µm) to 0.11 uL (D=1000 µm and H=140 µm), the number of cells approximately ranges from 200 to $1.1 \times 10^3$. To quantify the number of cells in the microparticles, fluorescent intensities were measured from the microparticles for 4 different heights and 6 different diameters, being proportional to the height. From these results, it was confirmed that the number of cells per unit area is almost linearly adjusted by the height of the PDMS templates. Meanwhile, it was known that other patterning methods seem to have a difficulty in adjusting the number density. FIG. 3D shows the calibration data that are calculated from the fluorescent intensities in FIG. 3C to provide a guideline to adjust the initial cell density of the microparticles. From the calibration result, the initial cell density was determined to be $10^9$ cells/mL for patterning and transferring process. Hereinafter, microparticles having a size of 140 µm high and 500 µm×500 µm squares were used for all experiments.

2. Quantitative Analysis of Response of Cells (Gene Expression Levels) Via Extracellular Induction The HPT method was first applied to extracellular induction experiments by patterning and transferring hydrogel-encapsulated cells on the agarose substrate that contains inducers such as acyl-homoserine lactone (AHL) or isopropyl-beta-D-thiogalactopyranoside (IPTG). This experiment is a basic identification experiment in which cells as a biosensor produced information, such as fluorescent signals, in response to external stimuli. For this experiment, two different plasmids that are engineered to express GFP were used. The first plasmid pTKU1-12R was electroporated into strain MG1655 so that the cells were activated to express GFP and referred to as "receiver cells" (RCs). As shown in FIG. 4A, the time-lapse image sequence obtained from the hydrogel-encapsulated RCs on the agarose hydrogel substrate that contained 10 nM AHL shows that the RCs start to express GFP in response to AHL, while it does not show any fluorescent intensities in the absence of AHL as control. In addition, the second plasmid pTrc99A-gfp was electroporated into the other strain DH10B. In the same manner, the time-lapse fluorescent image sequence was obtained from the hydrogel-encapsulated cells on the agarose hydrogel substrate that contained 1 mM IPTG. FIG. 4C shows the quantification of the average fluorescent intensities of 10 hydrogel microparticles that have negligible difference, meaning that this method enables reliable and accurate quantitative analysis. Both strains produce GFP continuously until 8 hours, and then they seem to stop the expression. Not only can this result be used for quantitative comparison of the gene expression levels that are caused by the different strains and inducers and result in about 1.5-fold difference (56 AU by AHL, 40 AU by IPTG). But, it also will be further applied to quantify gene copy number. Since expression levels typically depend on growth rates of the strains and culture conditions, the inventors of the present application performed a control experiment in which GFP-expressing cells (pTKU4-2) were patterned with different initial number densities ($10^7$, $10^8$, and $10^9$ cells/mL) on the agarose substrate, and their growths were monitored with time. As shown in FIG. 4D, the growth of the cells follows sigmoidal curves, and the fluorescent intensities of the cell approach the same value in the long run, regardless of the initial cell densities. This phenomenon is beneficial to quantitatively compare/analyze the expression levels of genetic circuits because the final number of cells in each microparticle is nearly the same. In addition, from the growth curves, it is confirmed that the agarose substrate provides sufficient nutrients with cells and maintains culture conditions properly for the extracellular induction/expression experiments. Cell growth appears to be saturated in 8 hours when the initial cell density is higher than $10^8$ cells/mL, but it seems to be retarded for a lower cell density.

As demonstrated in this experiment, it was confirmed that not only can the method be a very useful means to analyze the behavior/expression level of various genetic circuits in various strains with high accuracy but would also be further applied to the study of the extracellular responses of cells toward drugs, toxicity, antibiotics, etc.

3. Screening Multiple External Material and Quantitative Analysis of Cross-Talk Between Genes by Using Cells Having Two Genetic Circuits When the expression of several generic circuits by the individually inducing promoters is used, a biosensor may be developed by using simultaneous cell responses to several external stimuli/external materials. In addition, in terms of biology, when multiple inducing materials are applied, expression may be hindered from cross-talk between the promoters. However, the HPT method enabled the cross-talk between two synthetic genetic circuits to be investigated. Typically, two genetic circuits in a plasmid are easy to show crosstalk when they are chemically induced. However, it seems that the qualitative analysis still depends on a conventional tool like a microplate reader. To demonstrate the usefulness of the HPT method with respect to cross-talk quantitative analysis, a genetic circuit (pZBRG) that was designed to express GFP in the presence of tetracycline while RFP by arabinose was used. Using the HPT method, cells were patterned with the genetic circuit, and then transferred them on the agarose hydrogel substrate that contains only tetracycline, only arabinose, or both inducers, separately. First, in the presence of only tetracycline (1 µM), only GFP signals were detected, while in the presence of only arabinose (400 µM), only RFP signals were detected. On the other hand, in the presence of both tetracycline (1 µM) and arabinose (400 µM), the genetic circuits were simultaneously induced and, as a result, no significant cross-talk was observed (FIGS. 5A and 5B). FIG. 5C shows the quantification results of all separate experiments. For control experiment, the fluorescent intensities of GFP (filled symbols) and RFP (empty symbols) are nearly zero, while separate and simultaneous induction experiments show significant fluorescent intensities. However, the separate induction and simultaneous induction show a negligible difference in both RFP and GFP intensities.

The reason why no cross-talk phenomenon was observed can be attributed to the fact that two inducers have different molecular structures and weight, and the promoters are activated by different concentration ranges of inducers. The tet promoter (Ptet) is activated by the range of tetracycline from 1 nM to 1 µM while the araBAD promoter (PBAD) is activated by the range of arabinose from 6 µM to 400 µM. Herein, it was confirmed that the HPT method can quantitatively analyze the cross-talk between genetic circuits.

4. Quantitative Analysis of Cell Responses (Gene Expression Level) Using Inducer Concentration Gradients It would be very useful to test extracellular gene expression under multiple concentrations of inducers at a time. To investigate inducer concentration-dependent gene expression levels of cells in the alginate hydrogel patterns, concentration gradients of inducers were produced in the agarose hydrogel substrate. For this experiment, the RCs and the cells with pZBRG were reused. As shown in FIG. 6A, the RCs produce a fluorescent intensity gradient of GFP along the inducer concentration gradient of AHL. As a method of producing the concentration gradient, an agarose gel that contains high-concentration of inducer and an agarose gel that does not contain the inducer were stacked on left and right or up and down of the cell transferred area to form an inducer source and an inducer sink. Since the thickness of the gel is 1 mm or less, diffusion may quickly occur in a height direction (20 minutes, and in a lengthwise direction, a relatively long hour is required (10 hours). In addition, before and after 4 hours, the stacked agarose gel was replaced with newly fabricated gel to maintain the concentration gradient linearly for a long period of time (12 hours). Other than the gel stacking, wells may be formed on left and right or up and down of the cell transferred area and may be filled with a solution.

In addition, the HPT method may also allows generating concentration gradients of two inducers as illustrated in FIG. 6B. From left to right, an arabinose concentration gradient was generated in the same manner as the AHL. From right to left, a concentration gradient of tetracycline was generated. The fluorescent intensities of GFP and RFP were separately obtained, and then the two images were superposed to display both GFP and RFP intensities simultaneously. The leftmost column shows the strongest RFP intensities because the concentration of arabinose is highest. Meanwhile, the rightmost column shows the strongest GFP intensities because the concentration of tetracycline is the highest. The columns in the middle show both GFP and RFP. FIGS. 6C and 6D show quantification results of FIGS. 6A and 6B. For AHL, the GFP intensities at the high AHL concentration gradually increase with time, and their fluorescent intensity gradients are also well maintained up to 4 hours. However, after 4 hours, the fluorescent intensities at the low AHL concentration start to increase. This can be attributed to the fact that since the threshold concentration of AHL to trigger the plasmid is as low as sub-nM, the cells at the rightmost column can be easily contaminated by the random diffusion of AHL.

On the other hand, the threshold concentrations of arabinose and tetracycline are relatively high so that the gradients of the fluorescent intensities of GFP and RFP continuously get steeper over time, and then reach saturated values in about 10 hours. Accordingly, the HPT method according to an embodiment of the present invention enables not only quantification of inducer concentration-dependent gene expression of generic circuits, but also analysis of cross-talk under various concentrations of inducers.

5. Intercellular Communication Assays Using Hydrogel-Encapsulated Cell Patterns and Application into Biosensor for the Analysis of Target Cells.

As shown in FIG. 7, the agarose hydrogel substrate contains one type of cells in which the plasmid pTKU1-11S was electroporated, and these cells are referred to as "sender cells" (SCs). On the other hand, the alginate microparticle patterns contain the RCs that were used in the previous experiment. Three different initial densities of the SCs were used in the agarose hydrogel substrate in order to see the effect of the SC concentrations on the responses of the RCs. As shown in FIG. 7, no fluorescent intensities are observed in the absence of the RCs in the patterns (FIG. 7A, $10^9$ cells/mL of the SCs in the agarose substrate). Meanwhile, strong fluorescent intensities are shown in the presence of the RCs neighboring with the SCs. Interestingly, the highest SC concentration ($10^9$ cells/mL) makes the RCs give off weaker GFP intensities than the lowest SC concentration ($10^7$ cells/mL). FIG. 7B shows the quantification of the GFP intensities of the RCs for all SC densities. For the lowest SC density, the fluorescent intensities of the RCs gradually increase over 8 hours as the RCs grow. However, after 8 hours, the fluorescent intensities decrease because the growth of the RCs appears to be saturated while the SCs continue to grow. On the other hand, for the highest SC density, the RCs appear to express GFP for about 3 hours, and then the fluorescent intensities continuously decrease. As quantified in FIG. 4D, hydrogel-encapsulated cells ($10^9$ cells/mL) show their exponential growth phase between 4 and 6 hours after the cells are patterned and transferred on the agarose substrate. Therefore, it is more likely that the RCs neighboring the SCs at a low density ($10^7$ cells/mL) are induced to produce GFP later than those with the SCs at a high density ($10^9$ cells/mL).

In addition, the effect of nutrients on intercellular communication was investigated. Since the more SCs in the agarose substrate the more and the faster nutrients are consumed, the RCs neighboring with the SCs at a low density can grow better than those with the SCs at a high density. To verify the hypothesis, fluorescent intensities obtained from GFP-expressing cells in the alginate microparticles at a fixed density and RFP-expressing cells in the agarose substrate at 3 different densities as used before were quantified. For the lowest RFP-expressing cell density, GFP-expressing cells grow well and show similar growth curve as the RCs in FIG. 7B up to 8 hours. On the other hand, for the highest RFP-expressing cell density, GFP-expressing cells appear to grow only at the early stage (<4 hours), and then do not grow further, showing the similar growth behavior as the RCs in FIG. 7B. Interestingly, the RFP-expressing cells start to show the exponential growth phase in about 4 hours. Therefore, this result confirms that the SCs at the higher density consume more nutrients and impose a metabolic burden on the RCs earlier, resulting in low production of GFP. In addition, since the induction concentration of AHL is known to be very low, and AHL are very small molecules, AHL can diffuse quickly from the SCs to the neighboring RCs. As a result, the SCs at the lowest density appear to produce enough AHL to induce the RCs while nutrient consumption is minimized.

These results are completely consistent with previous study results. Therefore, it is believed that the HPT method facilitates the investigation of the cell-to-cell communication between two synthetically engineered cells successfully. In addition, the intercellular communication enables the development of a cell-based sensor that detects biological properties of a target cell in a substrate by using patterned cells. In the case of the cell-based biosensor, experiments and applications can be performed in the same manner as used to study intercellular communication described above.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A method of patterning and transferring of hydrogel-encapsulated cells, comprising:
   preparing a first substrate having a multiple hydrogel-encapsulated cell patterns, each of which comprising first cells and an alginate hydrogel, wherein the first substrate is formed by,
   forming a first mold having a photosensitive resin on the first substrate by soft lithography,
   preparing a second mold having a shape corresponding the first mold, followed by pouring a polymer thereinto and heat treating the result so as to form a polymer mold,
   filling the first cells simultaneously mixed with an alginate hydrogel solution into compartmentalized wells of the polymer mold,
   tilting the polymer mold to remove the excess of the solution, and
   gelating the multiple hydrogel-encapsulated cell patterns to provide the hydrogel-encapsulated cells by immersing the mixed first cells and the alginate hydrogel solution in a calcium solution,
   wherein the hydrogel-encapsulated cells form hydrogel microparticles,
   wherein each hydrogel-encapsulated cell pattern has a shape corresponding to each compartmentalized well of the polymer mold,
   wherein an aspect ratio (AR=diameter/height) of each hydrogel microparticle is greater than 1.25;
   preparing a second planar substrate comprising agarose hydrogel and any one of a second cell and a physiological active substance;
   transferring and placing the first substrate on the second planar substrate; and
   peeling off the polymer mold so that the hydrogel-encapsulated cells are left on the second planar substrate, wherein the hydrogel-encapsulated cells are compartmentalized on the second planar substrate.

2. The method of claim 1, further comprising, after the forming of the polymer mold, treating with oxygen plasma.

3. The method of claim 1, wherein the substrate is any one selected from the group consisting of silicon, glass, and methacrylate resin.

4. The method of claim 1, wherein the photosensitive resin is SU-8.

5. The method of claim 1, wherein the polymer is polydimethylsiloxane.

6. The method of claim 1, wherein the cells mixed with the alginate hydrogel solution are poured into the polymer mold to fill patterned microwells of which diameter ranged from 100 μm to 1000 μm.

* * * * *